US00RE40795E

(19) United States
(12) Reissued Patent
Ogihara et al.

(10) Patent Number: US RE40,795 E
(45) Date of Reissued Patent: Jun. 23, 2009

(54) PROCESS FOR PRODUCING 5-SUBSTITUTED OXAZOLE COMPOUNDS AND 5-SUBSTITUTED IMIDAZOLE COMPOUNDS

(75) Inventors: Atsushi Ogihara, Takaoka (JP); Hiroshi Sakai, Takaoka (JP); Nobuo Matsui, Ichihara (JP); Hidekazu Miyazaki, Takaoka (JP)

(73) Assignee: Nippon Soda Co., Ltd., Chiyoda-ku, Tokyo (JP)

(21) Appl. No.: 11/825,114

(22) PCT Filed: Mar. 20, 2002

(86) PCT No.: PCT/JP02/02704

§ 371 (c)(1), (2), (4) Date: Sep. 10, 2003

(87) PCT Pub. No.: WO02/076958

PCT Pub. Date: Oct. 3, 2002

Related U.S. Patent Documents

Reissue of:
(64) Patent No.: 7,102,010
Issued: Sep. 5, 2006
Appl. No.: 10/471,434
Filed: Mar. 20, 2002

(30) Foreign Application Priority Data

Mar. 23, 2001 (JP) ..... 2001-084092
Mar. 23, 2001 (JP) ..... 2001-084183
Mar. 23, 2001 (JP) ..... 2001-084184

(51) Int. Cl.
*C07D 263/02* (2006.01)
*C07D 233/00* (2006.01)
*C07D 263/30* (2006.01)

(52) U.S. Cl. ..... 548/215; 548/335.1; 548/235
(58) Field of Classification Search ..... 548/215, 548/335.1
See application file for complete search history.

(56) References Cited

U.S. PATENT DOCUMENTS 4,812,473 A * 3/1989 Kuwano et al.

FOREIGN PATENT DOCUMENTS

EP 0 776 894 A1 * 6/1997
JP 02-202871 * 8/1990

OTHER PUBLICATIONS

Aldrich Chemical Catalogue, pertinent page listing Tosmic and references, p. 2351, Year 2007–2008. This NPL was filed Feb. 1, 2008.*

Aldrich Chemical Catalogue, pertinent page listing Tosmic and references.*

Bheemashankar A. Kulkarini and A. Ganesan, "Solution–phase Parallel Oxazole Synthesis with TosMIC," Tetrahedron Letters, Institute of Moleular and Cell Biology, National University of Singapore (Singapore), p. 5637–5638.*

UNK, "Synthesis of tosmic from sodium–p–toluene sulfinale by onc pot method," p. 15–16, (Jan. 18, 1999).*

B.A. Kulkami, A. Ganesan, "Solution–phase parallel oxazole synthesis with tosmic" Tetrahedron Letters, XP004171530, Nlelsevier Science Publishers (Amsterdam), vol. 40 (No. 30), p. 5637–5638 (1999).*

Van Leusden, "Base–induced cycloaddition of sulfonylmethyl isocyanides to c,n double bonds," Journal of Organic Chemistry XP–002322151, USAmerican Chemical Society (Easton), vol. 42 (No. 7), p. 1153–1159, (1977).*

* cited by examiner

*Primary Examiner*—D. Margaret Seaman
*Assistant Examiner*—Nizal S Chandrakumar
(74) *Attorney, Agent, or Firm*—Darby & Darby P.C.

(57) ABSTRACT

A process for producing heterocyclic compounds which are useful as pesticides, drugs, fungicidal materials or intermediates thereof. TosMIC is reacted with an aldehyde or an imino compound: 1) in a solvent mixture of an aprotic solvent with a protic solvent in the presence of a base, 2) in the presence of a phase-transfer catalyst and an inorganic base, or 3) in the presence of an inorganic base. Thus, a desired product can be efficiently obtained using a solution without isolating TosMIC which is irritating and unstable, has a low decomposition point and shows explosivity.

8 Claims, No Drawings

PROCESS FOR PRODUCING 5-SUBSTITUTED OXAZOLE COMPOUNDS AND 5-SUBSTITUTED IMIDAZOLE COMPOUNDS

Matter enclosed in heavy brackets [ ] appears in the original patent but forms no part of this reissue specification; matter printed in italics indicates the additions made by reissue.

CROSS REFERENCE TO RELATED APPLICATIONS

*This application is a U.S. national phase application under 35 U.S.C. § 371 of International Patent Application No. PCT/JP02/02704, filed on Mar. 20, 2002, and claims the benefit of Japanese Patent Application Nos. 2001-84092, 2001-84183, and 2001-84184, all of which were filed on Mar. 23, 2001. The International Application was published in Japanese on Oct. 3, 2002, as International Publication No. WO 02/076958 A1 under PCT Article 21(2), the contents of which are incorporated herein by reference in its entirety.*

1. Field of the Invention

The present invention relates to processes for the preparation of heterocyclic compounds useful as excellent agricultural chemicals, drugs, functional materials or intermediates for producing them.

2. Background Art

A method of using an aldehyde and p-tolylsulfonylmethylisocyanide (hereinafter abbreviated as TosMIC) is generally known as a particularly useful process among those for synthesizing 5-substituted oxazole compounds. Generally, the process involves reacting an aldehyde with TosMIC in methanol in the presence of potassium carbonate. In addition, another known method involves the reaction in dimethoxyethane and methanol in the presence of an ion exchange resin (Ambersep 9000H-) (Tetrahedron Letters, 1972, 2369; Lect Heterocycl. Chem., 1980, (5), SI 11–122; Tetrahedron Letters, 1999, 5637–5638, and others).

Methods for synthesizing 5-substituted imidazoles with TosMIC are also known. Generally, an imino compound is reacted with TosMIC in an alcohol-type solvent in the presence of potassium carbonate (Tetrahedron Letters, 1976, 143–146; J. Org. Chem., Vol. 42 (7), [1997]*1977*, 1153–1159; Tetrahedron Letters, 2000, 5453–5456; and Tetrahedron, 53 (6), 2125–2136, 1997).

In all of the said processes, TosMIC is handled as crystals. Because of this, complicated isolation procedures including concentration, crystallization, separation of solvents, and drying are required, depending on the conditions, when the compound is produced industrially. Besides, a decrease in TosMIC production yield is unavoidable due to loss of product in filtrates. Furthermore, TosMIC is irritating, unstable and explosive with a low decomposition point. Its isolation should be avoided for safety reasons.

As described above, it is preferable not to isolate TosMIC when safety is taken into account. To handle TosMIC without isolating it, it is inevitable to use the reaction solution itself or a solution of another extract solvent after TosMIC is synthesized and post-treatments are done. It has been essential to develop safer processes for producing 5-substituted oxazoles and 5-substituted imidazoles with TosMIC in a solution without isolating it.

BRIEF SUMMARY OF THE INVENTION

It is an object of the present invention to provide safer and more efficient processes for the preparation of 5-substituted oxazoles and 5-substituted imidazoles.

The inventors studied in earnest to achieve this object, and found that a target compound could be obtained in good yield, even if TosMIC was used without isolation. TosMIC was reacted with an aldehyde or imino compound (1) in a mixed solvent of an aprotic solvent with a protic solvent in the presence of a base, (2) in the presence of a phase-transfer catalyst and an inorganic base, or (3) in the presence of an organic base.

In one aspect, the present invention relates to a process for the preparation of a 5-substituted oxazole or 5-substituted imidazole, characterized in that TosMIC is synthesized from N-(p-tolylsulfonylmethyl)formamide with phosphorus oxychloride, phosgene or diphosgene, and a tertiary amine, to form a TosMIC solution which is not isolated and purified as crystals, and reacting the TosMIC solution with an aldehyde or a compound represented by Formula [I]: $R^1CH{=}NR^2$ (wherein, $R^1$ and $R^2$ are optionally substituted phenyl, optionally substituted heterocyclic group or optionally substituted alkyl).

In some embodiments, the TosMIC solution is reacted with an aldehyde or a compound of Formula [I] in a mixed solvent of an aprotic solvent and a protic solvent in the presence of a base.

In some embodiments, the protic solvent is one or more solvents selected from the group consisting of water, $C_1$ to $C_{10}$ alcohols and mono- or poly-alkylene glycols.

In other embodiments, the aldehyde or the compound of Formula [I] is reacted with TosMIC in the presence of a phase-transfer catalyst and an inorganic base.

In some embodiments, the aldehyde or the compound of Formula [I] is reacted with TosMIC in the presence of an organic base.

In some embodiments, the organic base has a pKa of 12 or more.

In some embodiments, the the organic base is 1,8-diazabicyclo[5.4.0]undec-7-ene or 4-(N,N-dimethylamino) pyridine.

In other embodiments, the aldehyde is an unsubstituted or substituted aromatic aldehyde.

DETAILED DESCRIPTION OF THE INVENTION

Forms to implement the present invention are described in detail.

Aldehydes having any structure can be used for producing 5-substituted oxazoles in the present invention. Actual examples of preferred aldehydes include aldehydes having aromatic hydrocarbon groups such as phenyl, naphthyl or anthracenyl; and aldehydes having aromatic heterocyclic groups such as furyl, thienyl, oxazolyl, thiazolyl, pyridyl or N-methylpyrroloyl. These groups may be optionally substituted with various functional groups. Actual examples of such functional groups include halogen, optionally substituted alkyl, optionally substituted alkoxy, nitro, cyano, hydroxyl, optionally substituted amino and optionally substituted alkoxycarbonyl. Examples of alkyl groups include straight-chain or branched alkyl groups having 1 to 12 carbons, such as methyl, ethyl, n-propyl, i-propyl, n-butyl, s-butyl, i-butyl and t-butyl. Examples of alkoxy groups include straight-chain or branched, lower alkoxy groups having 1 to 4 carbons such as methoxy, ethoxy and propoxy. Further, examples of substituents of the functional groups include halogens, nitro, alkoxy and cyano.

In Formula [I] representing imino compounds, which are starting materials for producing 5-substituted imidazoles, $R^1$ and $R^2$ are the same or different. Actual examples of $R^1$ and $R^2$ include straight-chain or branched alkyl groups having 1 to 12 carbons, such as methyl, ethyl, n-propyl, i-propyl, n-butyl, s-butyl, i-butyl or t-butyl; aromatic hydrocarbons such as phenyl, naphthyl or anthracenyl; and aromatic heterocyclic groups such as furyl, thienyl, oxazolyl, thiazolyl, pyridyl or N-methylpyrroloyl. These groups may be optionally substituted with various functional groups. Actual examples of such functional groups include, for alkyl groups, halogen, optionally substituted alkoxy, nitro, cyano, hydroxyl, optionally substituted amino and optionally substituted alkoxycarbonyl. Examples of alkoxy groups include straight-chain or branched, lower alkoxy groups having 1 to 4 carbons such as methoxy, ethoxy and propoxy. Further, examples of substituents of the functional groups include halogens, nitro, alkoxy and cyano. Examples of substituents of aromatic hydrocarbon and aromatic heterocyclic groups include halogens, optionally substituted alkyl, optionally substituted alkoxy, nitro, cyano, hydroxyl, optionally substituted amino and optionally substituted alkoxycarbonyl. Examples of alkyl groups include straight-chain or branched alkyl groups having 1 to 12 carbons, such as methyl, ethyl, n-propyl, i-propyl, n-butyl, s-butyl, i-butyl and t-butyl. Examples of alkoxy groups include straight-chain or branched, lower alkoxy groups having 1 to 4 carbons such as methoxy, ethoxy and propoxy. Further, examples of substituents of the substituent groups include halogens, nitro, alkoxy and cyano.

An imino compound can be produced from a reaction of the corresponding aldehyde with an amine and be used without isolating and purifying it in the process of the present invention.

TosMIC produced by either of the generally applied methods described below can be used: N-(p-tolylsulfonylmethyl) formamide (TosMFA) is reacted with phosphorus oxychloride in dimethoxyethane (DME) (Organic Synthesis, Vol. 57, 102–106; Synthesis, 400–402 (1985); and Tetrahedron Letters, 1972, 2367), or a method using phosgene or diphosgene (Angew. Chem. Int. Ed. Engl. 16 (1997), 259; Angew. Chem., 77 (1965), 492; and DE 4032925).

Each of the processes is described in the following.

Process 1: Reaction of a TosMIC solution with an Aldehyde or a Compound of Formula [I] in a Mixed Solvent of an Aprotic Solvent and a Protic Solvent in the Presence of a Base.

Any organic and inorganic bases can be used as the base. Actual examples of organic bases include alkylamines such as dicyclohexylamine, diisopropylamine, diethylamine, triethylamine, tributylamine and diisopropylethylamine; alkylanilines such as N,N-dimethylaniline; heterocyclic amines such as piperidine, pyrrolizine, 2,2,6,6-tetramethylpiperidine, morpholine, piperazine, imidazole, 1-ethylpiperidine, 4-methylmorpholine, 1-methylpyrrolizine, 1,4-diazabicylo[2.2.2]octane and 1,8-diazabicyclo[5.4.0]-7-undecene; quarternary ammonium salts such as benzyltriethyl ammonium chloride and methyltrioctyl ammonium chloride; or diamines such as N,N,N',N'-tetramethylethylenediamine. Actual examples of inorganic bases include sodium hydroxide, potassium hydroxide, sodium carbonate, potassium carbonate, sodium hydrogen carbonate and potassium hydrogen carbonate.

It is preferable to use one or more solvents selected from the group consisting of water, $C_1$ to $C_{10}$ alcohols and mono- or poly-alkylene glycols as the protic solvent. Actual examples of protic solvents include water; alcohols such as methanol, ethanol and propanol; and glycols such as ethylene glycol, diethylene glycol and ethylene glycol monomethyl ether. Among them, methanol, ethylene glycol and 2-methoxyethanol are preferably used.

Preferred aprotic solvents are those that can be used for synthesizing or extracting TosMIC. Examples of aprotic solvents include halogen-type solvents such as methylene chloride, chloroform, dichloroethane and methylene chloride; aromatic hydrocarbon-type solvents such as benzene, chlorobenzene, toluene, xylene, nitrobenzene and benzonitrile; ester-type solvents such as methyl acetate, ethyl acetate and isopropyl acetate; ketone-type solvents such as acetone, methyl ethyl ketone, diethyl ketone and methyl isobutyl ketone; ether-type solvents such as diethyl ether and tetrahydrofuran; and polar solvents such as acetonitrile. Such solvents can be used alone or in any combination of two or more.

The reaction is carried out using 2.0 moles or more, preferably 2.0 to 2.5 moles, more preferably 2.0 to 2.2 moles, of a base per one mole of the aldehyde or compound of Formula [I]. Any amount of TosMIC can be used. It is preferably in the range of 0.8 to 1.5 moles, more preferably 0.9 to 1.2 moles per one mole of the aldehyde. Any amount of a protic solvent can be used if it can dissolve a base to some extent. It is favorable to use 1 liter or more per one mole of the aldehyde or compound of Formula [I] used. Any amount of an aprotic solvent can also be used if it dissolves TosMIC. An aprotic solvent can be mixed with a protic solvent at any mixing ratio. The ratio can be set at discretion.

In an exemplary reaction, an aldehyde or a compound of Formula [I] is mixed with a TosMIC solution and a base dissolved or suspended in a protic solvent, and reacted at a temperature from 0° C. to the boiling pint of the solvent used, preferably from 20 to 60° C. In this case, they can be reacted in the co-presence of a phase-transfer catalyst. The reaction is favorably carried out in a nitrogen stream or nitrogen atmosphere. The reaction time will differ depending on compounds to be reacted and reaction conditions. It is usually from about several minutes to 48 hours. After the reaction is completed, the reaction solution is cooled down, if necessary, and standard post-treatments yield the target compound.

Process 2: Reaction of an Aldehyde or a Compound of Formula [I] with TosMIC in the Presence of a Phase-Transfer Catalyst and an Inorganic Base.

Examples of phase-transfer catalysts suitable for use in the reactions of the present invention include onium salts such as quaternary ammonium salts and quaternary phosphonium salts, crown compounds and organic bases. Actual examples of quaternary ammonium salts include tetramethyl ammonium hydroxide, tetraethyl ammonium hydroxide, tetrabutyl ammonium hydroxide, trimethylbenzyl ammonium hydroxide, tetramethyl ammonium bromide, tetraethyl ammonium bromide, tetrabutyl ammonium bromide, triethylbenzyl ammonium bromide, trimethylphenyl ammonium bromide, tetramethyl ammonium chloride, tetraethyl ammonium chloride, tetrabutyl ammonium chloride, triethylbenzyl ammonium chloride, trimethylphenyl ammonium chloride, trioctylmethyl ammonium chloride, tributylbenzyl ammonium chloride, trimethylbenzyl ammonium chloride, N-lauryl pyridinium chloride, N-benzyl picolinium chloride, tricaprylmethyl ammonium chloride, tetramethyl ammonium iodide, tetrabutyl ammonium iodide and tetrabutyl ammonium sulfate. Examples of quaternary phosphonium salts include tetraethyl phosphonium chloride, tetraethyl phosphonium bromide, tetraethyl phosphonium iodide, tetrabutyl phosphonium bromide, tetraphenyl phosphonium bromide and triphenylbenzyl phosphonium bromide. Examples of crown compounds include crown ethers such as 15-crown-5,18-crown-6, and cryptands. Examples of organic bases include 1,8-diazabicyclo[5.4.0]undec-7-ene, 1,5-diazabicyclo[4.3.0]non-5-ene, 6-dibutylamino-1,8-diazabicyclo[5.4.0]undec-7-ene, triethylenediamine and N,N-dimethylaminopyridine. Any amount of a phase-transfer catalyst can be used. It is in a range of 0.0001 to 5 moles, preferably 0.01 to 0.5 equivalent moles per one mole of the aldehyde or compound of Formula [I] used.

Examples of inorganic bases suitable for use in the present invention include sodium hydroxide, potassium hydroxide, lithium hydroxide, potassium carbonate, sodium carbonate, potassium hydrogen carbonate and sodium hydrogen carbonate. Any amount of an inorganic base can be used. It is preferably between 0.5 and 10 moles, and more preferably 1.0 and 3 moles per one mole of the aldehyde used.

Actual examples of solvents suitable to use for the reaction include water; halogen-type solvents such as methylene chloride, chloroform and dichloroethane; aromatic hydrocarbon-type solvents such as benzene, toluene, xylene, benzonitrile, benzotrifluoride and chlorobenzene; ester-type solvents such as methyl acetate, ethyl acetate and isopropyl acetate; ketone-type solvents such as acetone, methyl ethyl ketone, diethyl ketone and methyl isobutyl ketone; ether-type solvents such as diethyl ether and tetrahydrofuran; and polar solvents such as acetonitrile. Particularly preferred are solvents that can be used for synthesizing TosMIC or extracting it after post-treatments. Examples include halogen-type solvents such as methylene chloride; aromatic hydrocarbon-type solvents such as toluene, xylene and chlorobenzene; ester-type solvents such as ethyl acetate; ketone-type solvents such as methyl isobutyl ketone; THF and acetonitrile. Such solvents can be used alone or in any combination of two or more. A mixed solvent of water with the exemplified solvents other than water is particularly preferred. Any amount of solvent can be used. Generally, the solvent is present in a range of 1 to 1,000 times by weight, preferably 5 to 100 times by weight, based on the weight of the aldehyde or compound of Formula [I] used.

In an exemplary reaction, an aldehyde or a compound of Formula [I] is mixed with TosMIC or its solution in an appropriate solution, and an inorganic base dissolved in water and a phase-transfer catalyst are added to react at a temperature ranging from 0° C. to the boiling point of the solvent used, preferably from 20 to 60° C. Any amount of TosMIC can be used. Preferably, the TosMIC is present in a range of 0.8 to 2.0 moles, more preferably 1.0 to 1.5 moles per one mole of the aldehyde or compound of Formula [I] used. The reaction is favorably carried out in a nitrogen stream or nitrogen atmosphere. The reaction time will differ depending on compounds to be reacted and other conditions, and is usually from several minutes to 48 hours. After the reaction is completed, the reaction solution is cooled down, if necessary, and standard post-treatments yield the target compound.

Process 3: Reaction of an Aldehyde or a Compound of Formula [I] with TosMIC in the Presence of an Organic Base.

Preferred organic bases for use have a pKa of 12 or more. Actual examples of organic bases include 1,8-diazabicyclo[5.4.0]undec-7-ene (DBU), 1,5-diazabicyclo[4.3.0]non-5-ene, 6-dibutylamino-1,8-diazabicylo[5.4.0]undec-7-ene, triethylenediamine, 4-(N,N-dimethylamino)pyridine (AP) and N,N,N',N'-tetramethylethylenediamine. Among them, DBU and AP are favorably exemplified. These can be used alone or as a mixture of two or more. The total amount of an organic base used is in a range of 0.9 to 10 moles, preferably 1.0 to 3.0 moles per one mole of the aldehyde or compound of Formula [I] used.

Examples of solvents suitable for use in the reaction of the present invention include halogen-type solvents such as methylene chloride, chloroform and dichloroethane; aromatic hydrocarbon-type solvents such as benzene, toluene, xylene, benzonitrile, benzotrifluoride and chlorobenzene; ester-type solvents such as methyl acetate, ethyl acetate and isopropyl acetate; ketone-type solvents such as acetone, methyl ethyl ketone, diethyl ketone and methyl isobutyl ketone; ether-type solvents such as diethyl ether and tetrahydrofuran; and polar solvents such as acetonitrile. Particularly preferred are solvents that can be used for synthesizing TosMIC or extracting it after post-treatments. Their examples include halogen-type solvents such as methylene chloride; aromatic hydrocarbon-type solvents such as toluene, xylene and chlorobenzene; ester-type solvents such as ethyl acetate; ketone-type solvents such as methyl isobutyl ketone; THF and acetonitrile. Such solvents can be used alone or in any combination of two or more. An amount of solvent used is in a range of 1 to 1,000 times by weight, preferably 5 to 100 times by weight, based on the weight of an aldehyde or a compound of Formula [I] used.

In an exemplary reaction, an aldehyde or a compound of Formula [I], a TosMIC solution and an organic base are dissolved and mixed in an appropriate solvent, and reacted at a temperature from −20° C. to the boiling point of the solvent used, preferably from 10 to 60° C. Any amount of TosMIC can be used. Preferably, the TosMIC is present in a range of 0.8 to 1.5 moles, more preferably 0.9 to 1.2 moles per one mole of the aldehyde or compound of Formula [I] used. The reaction is favorably carried out in a nitrogen stream or nitrogen atmosphere. A reaction time differs depending on compounds to be reacted and other conditions, and is usually from several minutes to 48 hours. After the reaction is completed, the reaction solution is cooled down, if necessary, and standard post-treatments yield the target compound.

These processes of the present invention can be applied when isolated crystalline TosMIC is used. They are favorably applied when TosMIC produced by reaction of TosMFA with phosphorus oxychloride, phosgene or diphosgene, and a tertiary amine, preferably with phosgene and a tertiary amine in an aprotic solvent, is used without isolating and purifying it.

Exemplification

The present invention is described in more detail in reference to Examples, but not limited to the examples.

EXAMPLE 1

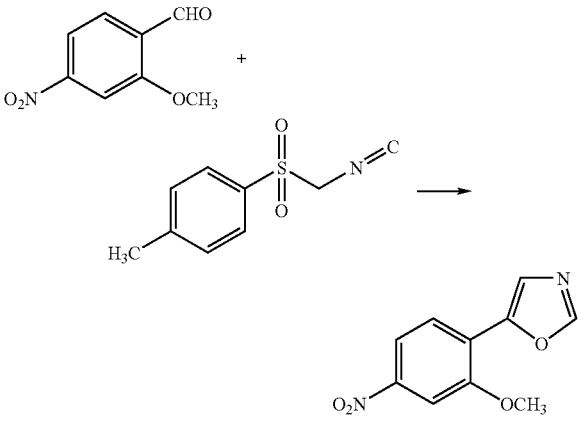

To 16 mL of methanol containing 3.1 g of potassium hydroxide were added 5.0 g of 2-methoxy-4-nitrobenzaldehyde and a methylene chloride solution containing 5.7 g of TosMIC at room temperature. The mixture was allowed to react at room temperature until high-performance liquid chromatography (HPLC) found no trace of the starting materials. Upon the completion of the reaction, the reaction solution was washed with water, and the solvents were distilled off. The target compound was crystallized from methanol and water, filtrated and dried to give 5.6 g of the compound (yield: 92%).

EXAMPLE 2

To 3.6 g of 2-methoxy-4-nitrobenzaldehyde and a toluene solution containing 4.1 g of TosMIC was added 20 mL of a methanol solution containing 2.3 g of potassium hydroxide at room temperature. The mixture was allowed to react at room temperature until HPLC found no trace of the starting materials. Upon the completion of the reaction, the reaction solution was washed with water. An HPLC analysis showed that the organic layer contained 4.2 g of the target compound (yield: 96%).

EXAMPLE 3

To 36 g of 2-methoxy-4-nitrobenzaldehyde and a chlorobenzene solution containing 43 g of TosMIC was added 200 mL of a methanol solution containing 23 g of potassium hydroxide at room temperature. The mixture was allowed to react at room temperature until HPLC found no trace of the starting materials. Upon the completion of the reaction, the reaction solution was washed with water. An HPLC analysis showed that the organic layer contained 39 g of the target compound (yield: 88%).

EXAMPLE 4

To 2 mL of ethylene glycol containing 0.24 g of potassium hydroxide was added 0.36 g of 2-methoxy-4-nitrobenzaldehyde at room temperature To this solution, 8.98 g of a methylene chloride solution containing 0.46 g of TosMIC was added dropwise. The mixture was allowed to react with stirring at room temperature until HPLC found no trace of the starting materials. Upon the completion of the reaction, the reaction solution was concentrated. An HPLC analysis showed that the concentrate contained 0.38 g of the target compound (yield: 86%).

EXAMPLE 5

To 2 mL of ethylene glycol containing 0.17 g of sodium hydroxide was added 0.37 g of 2-methoxy-4-nitrobenzaldehyde at room temperature. To this solution, 9.3 g of a methylene chloride solution containing 0.45 g of TosMIC was added dropwise. The mixture was allowed to react with stirring at room temperature until HPLC found no trace of the starting materials. Upon the completion of the reaction, the reaction solution was concentrated. An HPLC analysis showed that the concentrate contained 0.36 g of the target compound (yield: 82%).

EXAMPLE 6

140.2 g (0.65 mol) of N-(4-methylbenzenesulfonylmethyl)-formamide and 1.3 L of methylene chloride were placed in a reaction vessel, and kept below 5° C. by cooling in an ice bath. Then, 82.2 g (0.85 mol, molar ratio: 1.3) of phosgene was bubbled into the solution over 30 minutes, followed by adding 138.6 g (1.4 mol, molar ratio: 2.1) of triethylamine diluted with 195 mL of methylene chloride into the solution dropwise over 30 minutes at the same temperature. To the obtained orange-colored reaction solution was added 28 g (molar ratio: 0.3) of a 28% aqueous solution of sodium hydroxide diluted with 1.5 L of water. The resulting solution was stirred at about 5° C. for 30 minutes. The solution was separated by a separating funnel to give 2096.0 g of the organic layer. A quantitative HPLC analysis showed that the organic layer contained 111.3 g of TosMIC (yield: 88%). (Step 1)

98.4 g of 2-methoxy-4-nitrobenzaldehyde was dissolved in 552 mL of ethylene glycol containing 71.2 g of potassium hydroxide and 110 mL of methylene chloride, heated to 42 C, and added to the methylene chloride solution containing 111.3 g of TosMIC that was obtained in Step 1. The mixture was allowed to react at 42° C. until HPLC found no trace of the starting materials. Upon the completion of the reaction, the reaction solution was separated. The methylene-chloride layer was washed with water. The solvents were distilled off. The target compound was crystallized from methanol and water, filtrated and dried to give 102.4 g of the compound (yield: 86%). (Step 2)

EXAMPLE 7

530 mL of methanol containing 75.1 g of potassium hydroxide was added at room temperature to a chlorobenzene solution containing 110 g of TosMIC with 97 g of 2-methoxy-4-nitrobenzaldehyde added. The mixture was kept reacting at 42° C. until HPLC found no trace of the starting materials. Upon the completion of the reaction, the reaction solution was separated. The chlorobenzene layer was washed with water. The solvent was distilled off. The target compound was crystallized from chlorobenzene, filtrated and dried to give 103.4 g of the compound (yield: 87.7%).

EXAMPLE 8

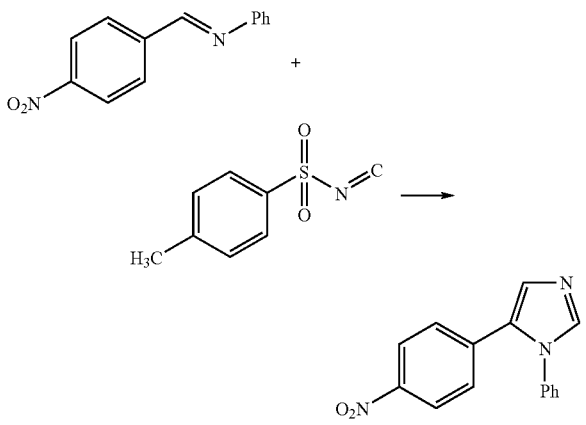

To 19.7 g of a methylene chloride solution containing 0.99 g of TosMIC was added 1.10 g of p-nitrobenzylidene aniline. To the resulting solution, 5 mL of methanol containing 0.70 g of potassium hydroxide was added dropwise. The mixture was allowed to react with stirring at room temperature until HPLC found no trace of the starting materials. Upon the completion of the reaction, the reaction solution was washed with water and concentrated. The target compound was recrystallized from methanol, filtrated and dried to give 0.78 g of the compound. An analysis showed that the filtrate contained 0.31 g of the compound (yield: 83%).

EXAMPLE 9

0.24 g of potassium hydroxide was added to 2 mL of ethylene glycol and 2 mL of methylene chloride, and heated to dissolve. To this solution, 8.66 g of a methylene chloride solution containing 0.46 g of TosMIC with 0.36 g of 2-methoxy-4-nitrobenzaldehyde dissolved was added dropwise. The mixture was heated to 42° C. and allowed to react until HPLC found no trace of the starting materials. Upon the completion of the reaction, the ethylene-glycol layer and methylene-chloride layer were separated. The latter was concentrated to give 0.41 g of the target compound (yield: 93%).

EXAMPLE 10

Preparation of 5-(2-methoxy-4-nitrophenyl)oxazole

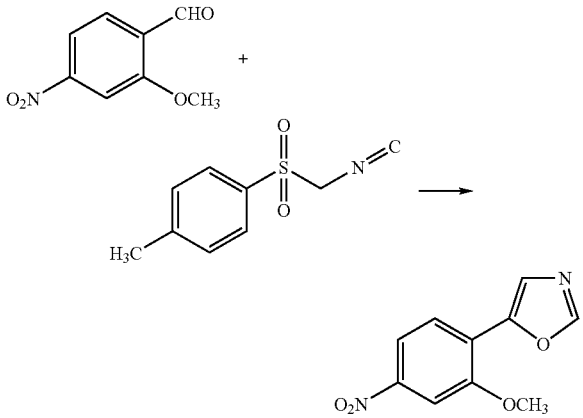

To an aqueous solution containing 0.16 g of sodium hydroxide were added 0.36 g of 2-methoxy-4-nitrobenzaldehyde, 8.1 g of a methylene chloride solution containing 0.43 g of TosMIC which was obtained in the same way as Step 1 of Example 6 and 0.08 g of DBU at room temperature. The mixture was heated to 40° C. and kept reacting until HPLC found no trace of the starting materials. Upon the completion of the reaction, the reaction solution was cooled down to room temperature, washed with water and dried over anhydrous magnesium sulfate. The solvents were distilled off. An HPLC analysis showed that the concentrated residue contained 0.37 g of the target compound (yield: 85%).

EXAMPLE 11

Preparation of 5-(4-nitrophenyl)oxazole

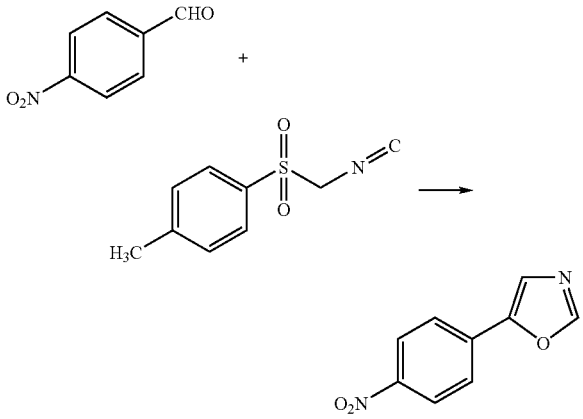

To an aqueous solution containing 0.84 g of sodium hydroxide were added 0.45 g of 4-nitrobenzaldehyde, 12.2 g of a methylene chloride solution containing 0.65 g of TosMIC which was obtained in the same way as that of Example 6 and 0.10 g of tetrabutyl ammonium bromide at room temperature. The mixture was allowed to react at room temperature until HPLC found no trace of the starting materials. Upon the completion of the reaction, the reaction solution was washed with water and dried over anhydrous magnesium sulfate. The solvents were distilled off. An HPLC analysis showed that the concentrated residue contained 0.82 g of the target compound (yield: 93%).

EXAMPLE 12

To 0.36 g of 2-methoxy-4-nitrobenzaldehyde and 8.5 g of a methylene chloride solution containing 0.45 g of TosMIC which was obtained in the same way as that of Example 6 was added 0.60 g of DBU at room temperature. The mixture was allowed to react at room temperature until HPLC found no trace of the starting materials. Upon the completion of the reaction, the reaction solution was washed with water and dried over anhydrous magnesium sulfate. The solvent was distilled off. An HPLC analysis showed that the concentrated residue contained 0.47 g of the target compound (yield: 96%).

APPLICABILITY IN INDUSTRY

As described above, according to the process of the present invention, 5-substituted oxazoles and 5-substituted imidazoles, which are useful as agricultural chemicals, drugs, functional materials, and others and as intermediates to produce them, can be prepared safely and efficiently.

What is claimed:

1. A process for the preparation of a 5-substituted oxazole or 5-substituted imidazole comprising synthesizing p-tolylsulfonylmethylisocyanide from N-(p-tolylsulfonylmethyl)formamide with phosphorus oxychloride, phosgene or diphosgene, and a tertiary amine, to form a p-tolylsulfonylmethylisocyanide solution which is not isolated and purified as crystals,

*washing the p-tolylsulfonylmethylisocyanide solution with an aqueous alkaline solution,* and reacting the p-tolylsulfonylmethylisocyanide solution with an aldehyde or a compound represented by Formula (I):

$$R^1CH{=}NR^2$$

wherein, $R^1$ and $R^2$ are optionally substituted phenyl, optionally substituted heterocyclic group or optionally substituted alkyl, wherein the p-tolylsulfonylmethylisocyanide solution is reacted with an aldehyde or a compound of Formula (I) in a mixed solvent of an aprotic solvent and a protic solvent in the presence of potassium hydroxide or sodium hydroxide or mixtures thereof.

2. A process according to claim 1 in which the protic solvent is one or more solvents selected from the group consisting of water, $C_1$ to $C_{10}$ [alcohols and mono- or] *alcohols, mono-alkylene glycols and* poly-alkylene glycols.

3. A process for the preparation of a 5-substituted oxazole or 5-substituted imidazole comprising synthesizing p-tolylsulfonylmethylisocyanide from N-(p-tolylsulfonylmethyl) formamide with phosphorus oxychloride, phosgene or diphosgene, and a tertiary amine, to form a p-tolylsulfonylmethylisocyanide solution which is not isolated and purified as crystals,

*washing the p-tolylsulfonylmethylisocyanide solution with an aqueous alkaline solution,* and reacting the p-tolylsulfonylmethylisocyanide solution with an aldehyde or a compound represented by Formula (I):

$$R^1CH{=}NR^2$$

wherein, $R^1$ and $R^2$ are optionally substituted phenyl, optionally substituted heterocyclic group or optionally substituted alkyl, wherein the aldehyde or the compound of Formula [I] is reacted with p-tolylsulfonylmethylisocyanide in a mixed solvent of an aprotic solvent and water in the presence of *an inorganic base and* between about 0.0001 moles and about 5 moles of at least one phase-transfer catalyst selected from the group consisting of quaternary ammonium [salts and] *salts,* quaternary phosphonium [salts and an inorganic base,] *salts, crown compounds and organic bases*.

4. A process for the preparation of a 5-substituted oxazole or 5-substituted imidazole comprising synthesizing p-tolylsulfonylmethylisocyanide from N-(p-tolylsulfonylmethyl) formamide with phosphorus oxychloride, phosgene or diphosgene, and a tertiary amine, to form a p-tolylsulfonylmethylisocyanide solution which is not isolated and purified as crystals,

*washing the p-tolylsulfonylmethylisocyanide solution with an aqueous alkaline solution,* and reacting the p-tolylsulfonylmethylisocyanide solution with an aldehyde or a compound represented by Formula (I):

$$R^1CH{=}NR^2$$

wherein, $R^1$ and $R^2$ are optionally substituted phenyl, optionally substituted heterocyclic group or optionally substituted alkyl, wherein the aldehyde or the compound of Formula [I] is reacted with p-tolylsulfonylmethylisocyanide *in halogen-type solvents, aromatic hydrocarbon-type solvents, ester-type solvents, ketone-type solvents, ether-type solvents, or polar solvents* in the presence of an organic base which has a pKa of 12 or more.

5. A process according to claim 4 in which the organic base is 1,8-diazabicyclo[5.4.0]undec-7-ene or 4-(N,N-dimethylamino)pyridine.

6. The process according to claim 1 wherein the aldehyde is an unsubstituted or substituted aromatic aldehyde.

7. The process according to claim 3 wherein the aldehyde is an unsubstituted or substituted aromatic aldehyde.

8. The process according to claim 4 wherein the aldehyde is an unsubstituted or substituted aromatic aldehyde.

* * * * *